United States Patent [19]

Goldsmith

[11] Patent Number: 5,407,421
[45] Date of Patent: Apr. 18, 1995

[54] COMPRESSIVE BRACE

[76] Inventor: Seth Goldsmith, 3326 E. Overlook, Apt. #3, Cleveland, Ohio 44118

[21] Appl. No.: 246,345

[22] Filed: May 18, 1994

[51] Int. Cl.[6] .......................... A61F 5/00; A61F 5/37
[52] U.S. Cl. .......................................... 602/5; 602/13; 602/14; 602/23; 602/26; 128/882; 607/114
[58] Field of Search ............... 128/882, 869, DIG. 15, 128/DIG. 20; 602/5, 13, 14, 23, 26; 607/114

[56] References Cited

U.S. PATENT DOCUMENTS

| | | | |
|---|---|---|---|
| 2,113,253 | 4/1938 | Grey . | |
| 2,699,165 | 1/1955 | Ferrier | 128/DIG. 20 |
| 3,548,819 | 12/1970 | Davis | 602/14 |
| 3,561,435 | 2/1971 | Nicholson . | |
| 3,717,145 | 2/1973 | Berndt | 602/14 |
| 3,862,629 | 1/1975 | Rotta | 128/DIG. 20 |
| 3,901,225 | 8/1975 | Sconce | 128/DIG. 13 |
| 3,901,225 | 8/1975 | Scone . | |
| 4,013,069 | 3/1977 | Hasty . | |
| 4,030,488 | 6/1977 | Hasty . | |
| 4,033,337 | 7/1977 | Raczkowski | 128/DIG. 20 |
| 4,039,039 | 8/1977 | Gottfried . | |
| 4,280,489 | 7/1981 | Johnson . | |
| 4,592,358 | 6/1986 | Westplate . | |
| 4,628,945 | 12/1986 | Johnson . | |
| 4,753,241 | 6/1988 | Brannigan . | |
| 4,846,176 | 7/1989 | Golden . | |
| 4,886,063 | 12/1989 | Crews . | |
| 4,993,409 | 2/1991 | Grim . | |
| 5,020,711 | 6/1991 | Kelley | 607/114 |
| 5,025,781 | 6/1991 | Ferrari | 128/DIG. 20 |
| 5,088,478 | 2/1992 | Grim . | |
| 5,117,812 | 6/1992 | McWhorter . | |
| 5,125,400 | 6/1992 | Johnson . | |

OTHER PUBLICATIONS

*Journal of Bone Joint Surgery,* 1974, 56 (Dec. 1586-1591).
*The Journal of Athletic Training,* 1992; 27: 235-237.

Primary Examiner—Michael A. Brown

[57] ABSTRACT

The brace includes one or more air inflatable bladders equipped with an automatic, regulated, and removable air pressure regulation valve, where different valves have different release settings. In addition, a removable, thermally responsive material for hot and cold therapy may be placed in a pocket between the outer and inner material for the brace. The inside surface of the brace is comprised of an absorbent material that absorbs body perspiration, and then releases it to the atmosphere. The brace is placed around the injured area of the patient so that the air bladder(s) lies against the injured area. Air is then introduced into the air bladder via an air inlet valve, forming a compressive force on the body part in contact. In another embodiment of the brace, pneumatic compression is obtained by the use of two or more overlapping air inflatable bladders, each having an air regulation valve with a different pressure release level, wherein the pressure is higher distally and lower ventrally.

8 Claims, 3 Drawing Sheets

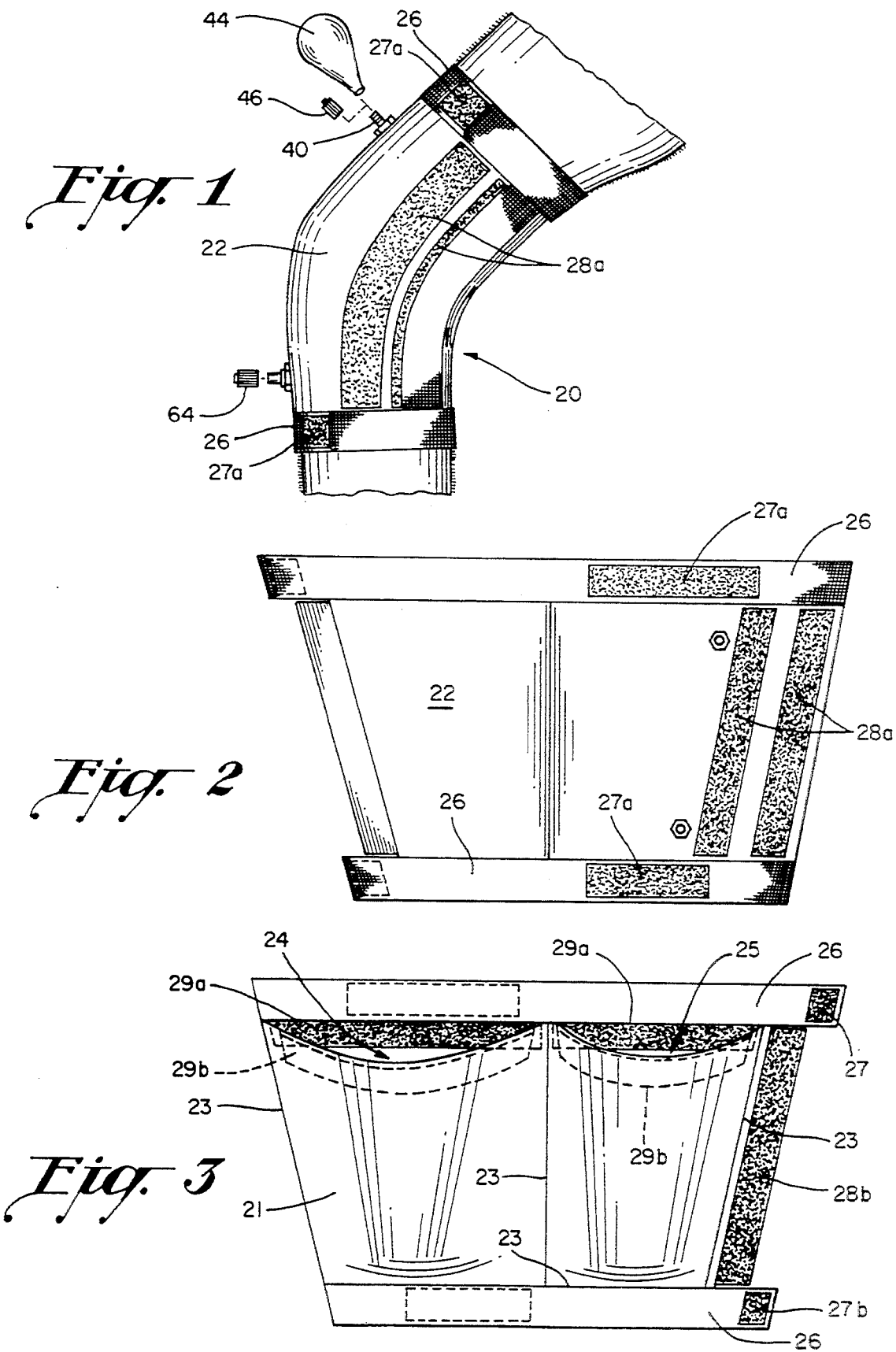

COMPRESSIVE BRACE

FIELD OF THE INVENTION

The present invention relates to a therapeutic device using compression, with or without heat and cold, in medical treatment. More particularly, the invention relates to a novel wrap that has one or more flexible, air-inflatable bladders that, when inflated, provide pressure to the injured area, where the pressure is regulated by automatic, air pressure regulation valves.

BACKGROUND OF THE INVENTION

Cold, compression, elevation and heat have become widely recognized as the standard care for acute musculoskeletal injuries. Of these measures, compression seems to be the most effective deterrent to swelling. (*The Physician and Sports Medicine*, 1985; 6 (June): 97–106) Applying external compression inhibits seepage of fluid into underlying tissue spaces and disperses excess fluid. Cold reduces swelling, bleeding, and inflammation by constricting blood vessels, slowing cell metabolism, and inhibiting the inflammatory response. Heat, on the other hand, causes vasodilation, which increases blood flow and accelerates the removal of waste products.

The use of compression and hot/cold therapy for the treatment of injury and illness such as the reduction of post surgery edema, musculoskeletal injuries, including trauma, sprains, strains, ligament and tendon damage, and their use in the treatment of arthritis, pain control, respiratory and circulatory problems have been well documented.

There are numerous devices which are designed to cool or heat a bodily injury, by holding a therapeutic thermopack adjacent an injured limb, as described in U.S. Pat. Nos. 5,020,711 to Kelly, 4,592,358 to Westplate and 4,886,063 to Crews.

These devices all have the disadvantage that they do not deliver an adequate therapeutic effect to the appropriate anatomical areas. Some are bulky and non-portable, while others tend to slip out of position due to their shape and design, requiring the patient to be relatively immobile while wearing them. Failure of the compress to conform slowly and to retain close contact once positioned, results in irregular heating and cooling of the skin area. The problem often results in irregular or non-uniform healing of the skin, increased swelling, and the like.

To overcome this problem, devices are available which incorporate a plurality of small cells interconnected by passageways. For example, U.S. Pat. Nos. 4,753,241 to Brannigan and 4,846,176 to Golden disclose a temperature maintaining device consisting of an upper surface of a flexible material that is sealed to a lower surface of flexible material to form a plurality of chambers and interconnected passageways. The chambers and passageways are filled with a thermal responsive medium used to heat or cool the body.

Despite their tendency to cool or heat the body, even these newer wraps had drawbacks which have prevented them for attaining widespread acceptance. For instance, most of the previous wraps include rather complex interior structures for maintaining the cold pack in a central position. These complex structures require time-consuming manufacturing procedures and increase the overall cost of the product. In addition, the wraps are generally not washable, and thus become dirty and perspiration-soaked after several wearings.

Recent medical studies suggest that ice has a more limited role in the reduction of swelling as compared to external compression. (*Journal of Bone Joint Surgery*, 1974; 56 (December) 1586–1591) Therefore, physicians, physical therapists, and athletic trainers have placed more importance on compression therapy.

Various compression devices utilize air compression with one or more inflatable bladders that form a compressive-force upon the injured area. These include U.S. Pat. Nos. 4,280,489, 4,628,945 and 5,125,400.

Other compression devices utilize both an air inflatable bladder and a thermally responsive medium, where the air bladder is positioned outside the thermal medium to provide a uniform compressive force upon the thermal medium and the injured body part.

U.S. Pat. No. 4,993,409 to Grim discloses a back support consisting of a thermally responsive gel bladder with three air inflatable chambers positioned outside the gel bladder to provide a compressive force upon the lower back.

U.S. Pat. No. 5,088,478 to Grim discloses an ankle brace worn under a shoe, that has a gel bladder with a second bladder inflatable with air positioned outside the first bladder to provide a uniform compressive force upon the bladder filled with gel.

U.S. Pat. Nos. 3,901,225 to Scone, 3,561,435 to Nicholson, and 3,548,819 to Davis disclose air inflatable splints with an air bladder positioned outside a removable thermo pack, where the air bladder provides a compressive force upon the thermo pack which braces and conforms the device.

The inability to measure or control compression levels—a disadvantage of all existing air-inflatable splints and braces—can lead to over pressure and injury or under pressure and inadequate treatment. Over pressurization can cause skin ischemia, loss of blood circulation, and increased trauma. In addition, excessive compression over a cold medium has been known to cause nerve damage. (*The Journal of Athletic Training*, 1992; 27: 235–237)

To alleviate these problems, air compression braces and splints were designed with pressure monitors. These include U.S. Pat. Nos. 2,699,165 to Ferrier, 2,113,253 to Grey, and 4,039,039 to Gottfried.

The problem with these air compression braces is that they all utilize external pressure monitoring devices that are bulky, non-portable, and involve complex manufacturing processes. These devices are primarily used by patients who are bedridden or immobile.

Another embodiment of a compression brace is disclosed in U.S. Pat. No. 5,025,781 which has a bleed hole that continuously releases pressure. The problem with this device is that it cannot keep a constant pressure and relies on an external electric pump to re-pressurize.

Another embodiment of a compression brace having an external pump source is the sequential pneumatic pressure sleeve. Sequential compression is used because of its ability to provide a graduated application of pressure, i.e., greater pressure to the lower leg and reduced pressure to the upper leg. Devices with the foregoing description are disclosed in U.S. Pat. Nos. 4,013,069 and 4,030,488 to Hasty, and 5,117,812 to McWhorter.

These braces all have the disadvantages that they require an external, electric pump to provide the compression. The pump is bulky, relatively non-portable, involves complex manufacturing and is expensive.

Another disadvantage of the above-mentioned patents is that they do not provide for the unrestricted movement of the joint through its full range of motion. The air bladders stiffen the brace and restrict or hinder the free movement of the joint.

SUMMARY OF THE INVENTION

An important object of the present invention is to provide pressure regulation valves that are removable and interchangeable. The valves can either screw or pressure fit into a flange that forms an air tight seal onto the air inflatable bladder.

Another object is to provide pressure regulation valves that have different pressure regulation settings. The invention includes a variety of valves, wherein the user of the invention can use different valves for different applications. In other words, the user of the invention can change valves, and thus change the compression setting of the brace. For example, when utilizing the thermal bladder, a low pressure valve would be used for cold therapy. This valve will provide just enough pressure to achieve a uniform surface contact between the brace and the user's skin without over compressing the injured area. Thus, the brace provides maximum thermal transfer with minimal compression. This is very important, as excessive compression over cold can cause never damage. When the hot or cold therapy is completed, the thermal bladder can be removed and the brace can be worn as a pressure sleeve. At this point, if higher pressure is desired, the low pressure regulation valve can be removed, and a higher pressure regulation valve inserted in its place. As the injury progresses, different valves can be inserted, providing different compression levels. Therefore, not only does the invention provide the optimal compression levels for hot and cold therapy, but it also provides the optimal compression levels for the ongoing treatment of the injury with compression therapy.

Another object is to provide an absorbent inside material that lies adjacent to the user's skin and absorbs the user's perspiration. The moisture then travels down the inside material to the edge of the brace, where it evaporates into the surrounding atmosphere.

Another object is to provide a uniform compressive force that is applied to the body part in contact. A compressive force on the thermo bladder is provided by the air bladder, which in turn applies a compressive force on the user's skin, enabling a uniform and more complete surface contact, thus providing uniform heating or cooling, and equal pressure to the entire body portion in contact.

Another object is to provide a removable thermal bladder that can be heated or cooled and reattached to the brace.

Another object is to provide a design for a specific body part that conforms to the joint or body part and thus limits the range of motion of the patient.

Another object is to provide an improved pneumatic brace, having means for applying a graduated application of pressure to the body part in contact. The use of a stronger pressure regulation valve distally and then continuously weaker pressure release valves ventrally accomplishes this goal.

Another object is to provide stiff plastic or metal stays that further limit the range of motion of the joint.

Yet another object is to provide separate air bladders that overlap, so as the patient flexes and extends the joint, the air bladders freely slide past one another permitting unrestricted movement of the joint, and uninterrupted compression.

A still further object is to provide foam pad inserts that provide for non-circumferential compression by having channels in the foam that have no compression, allowing for the unrestricted flow of lymphatic fluid through the non-compressed passages, and away from the injured site.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings preferred embodiments thereof, from an inspection of which, when considered in connection with the following description, the invention, its construction and operation, and many of its advantages should be readily understood and appreciated.

FIG. 1 depicts one embodiment of a brace incorporating the features of the present invention, applied to a person's knee;

FIG. 2 is a plan view of one side of the brace of FIG. 1, in its open condition, prior to application to a knee;

FIG. 3 is a plan view of the other side of the brace in its open condition, prior to application to a knee;

DETAILED DESCRIPTION OF THE PREFERRED EMBODIMENTS

Figure 4:
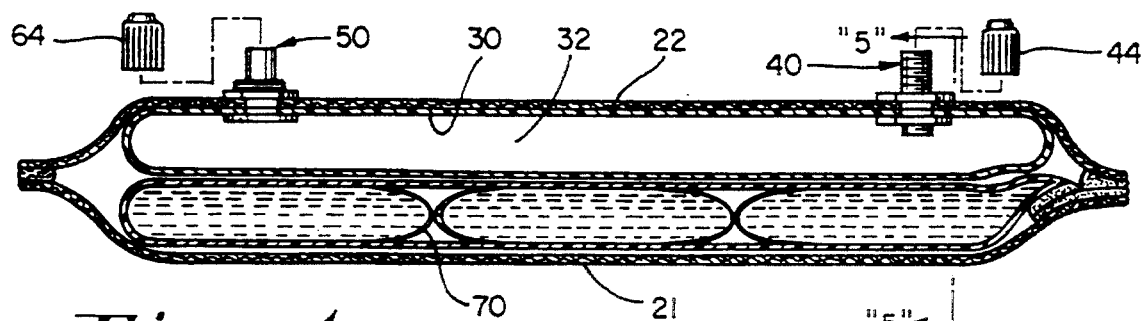
FIG. 4. is an enlarged view in section taken longitudinally through one of the pockets of the brace, containing an air bladder and a thermal bladder depicted in section.

Referring now to the drawings, and more particularly to FIG. 1, there is depicted a brace 20 incorporating the features of the present invention. Brace 20 is specifically designed to be applied to a particular body part, namely one's knee. However, by changing the particular design, and still incorporating the features of the present invention, the brace can be made to be applied to other body parts.

Referring to FIGS. 2 and 3, brace 20 comprises a flexible inner sheet 21 and a flexible outer sheet 22 sealed along lines 23 to create two pockets 24 and 25. Sheet 21 is composed of an absorbent material, and sheet 22 is composed of an insulating material. Although the particular embodiment depicted in FIGS. 2 and 3 has two pockets 24 and 25, a brace with a single pocket 25 can be provided instead. Attached to the top and bottom of sheet 22 and extending laterally with respect thereto, are narrow elastic webbings 26. To hold brace 20 in place on one's knee, there are provided Velcro-like fastening systems, each including a hook means and a loop means. On the outer surface of each webbing 26 near one side is a strip 27a of hook means. On the inner side of each webbing 26 at the other side is a patch 27b of loop means. On outer sheet 22, near one side thereof, are two strips 28a of hook means. On inner sheet 21, near the other side thereof, is a strip 28b of loop means.

A Velcro-like fastening system is also used to close pockets 24 and 25. On the outside surface of inner sheet 21 are two strips 29b of loop means. On the inside surface of outer sheet 22 are strips 29a of hook means.

Inserted in each of pockets 24 and 25 are a pressure bladder and, preferably, a thermal bladder, as will be described. In the case of a brace with a single pocket 25, an air bladder and, preferably, a thermal bladder are inserted therein. The fastening system including strips 29a and 29b are closed. Brace 20 is wrapped around the knee, as depicted in FIG. 1, and the Velcro-like fastening systems are closed, by engaging strip 28b with a selected one of strips 28a and by engaging patches 27b respectively with strips 27a.

Figure 5:
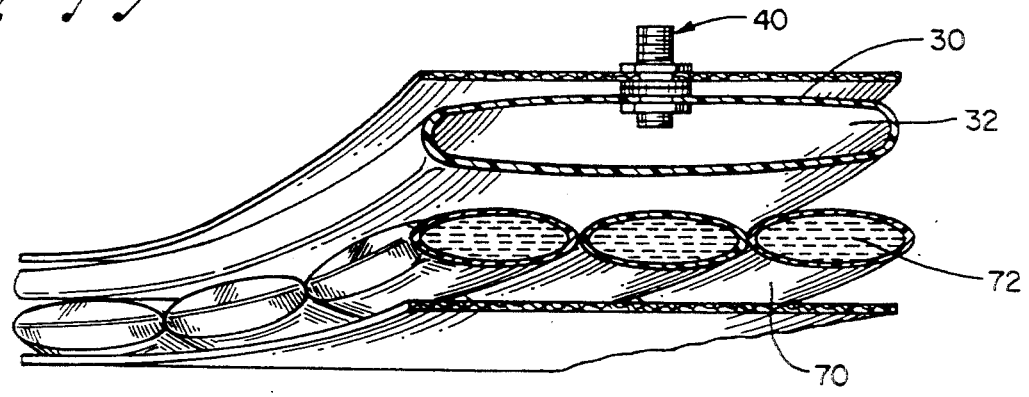
FIG. 5 is a view in section taken along lines 5—5 of FIG. 4.
Figure 9:
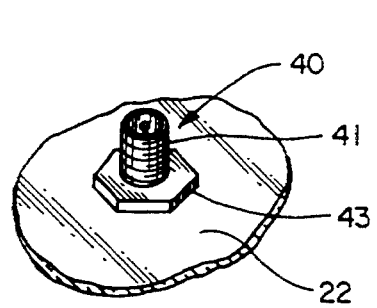
FIG. 9 is a perspective view of the air-admitting valve, with the outer sheet being shown as a fragment.
Figure 10:
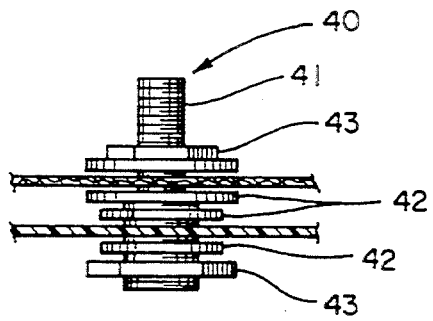
FIG. 10 is an elevational view of the air-admitting valve with the pocket and the air bladder shown in section.

Referring to FIGS. 4 and 5, air bladder 30 is a thin sheet of polyethylene or the like sealed to define a hermetically sealed chamber 32. An inlet valve 40 is attached to sheet 22 and to air bladder 30. It is through valve 40 that gas, such as air, under pressure, is admitted into chamber 32. Referring to FIGS. 9 and 10, valve 40 includes a threaded body 41 and a series of washers 42 and nuts 43, to enable attachment to sheet 22 and to air bladder 30. Bladder 30 is filled with air such as by using hand bulb 44 (FIG. 1). A cap 46 (FIG. 4) is applied after bladder 30 is filled with air. The depicted manner of attaching valve 40 is exemplary. Such attachment can be accomplished in a variety of other ways, such as heat sealing, welding, gluing, clamping or the like.

Figure 6:
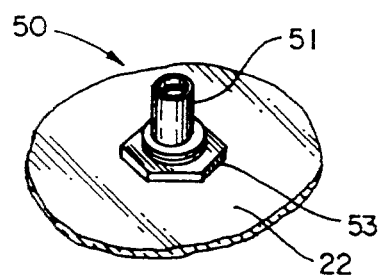
FIG. 6 is a perspective view of the pressure-maintaining valve, with the outer pocket sheet shown as a fragment.
Figures 7, 8:
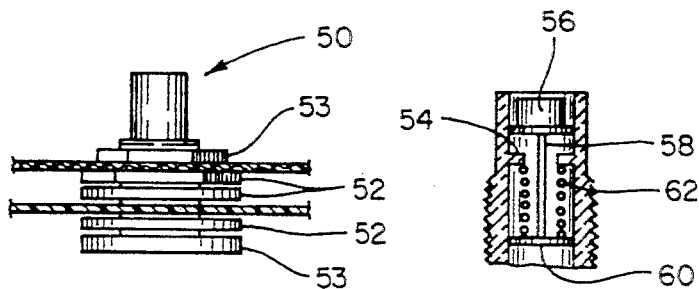
FIG. 7 is an elevational view of the pressure maintaining valve with the pocket and the bladder shown in section.
FIG. 8 is a sectional view taken through the pressure-maintaining valve.

Referring to FIGS. 6–8, brace 20 further comprises a pressure-maintaining valve 50 having a body 51. Valve 50 is attached at a different location, to sheet 22 and to air bladder 30, using washers 52 and nuts 53. Referring to FIG. 8, valve 50 includes a seat 54. A sealing member 56 has a stem 58 which in turn carries an abutment 60. A spring 62 located between seat 54 and abutment 60 urges sealing member 56 to a closed position. When the pressure in air bladder 30 exceeds a predetermined amount, as established by the force of spring 62, valve 50 will open and air will be released until the pressure within air bladder 30 is equalized with the force of spring 62, whereupon valve 50 once again closes. A cap 64 is supplied to close valve 50.

Valve 50 is readily removable and replaceable with a valve 50 having a spring exerting a different force. Brace 20 may be supplied with a plurality of such valves respectively corresponding to a plurality of predetermined pressures so that the pressure in air bladder 30 can be selected. Thus, with one valve 50, air pressure in air bladder 30 is X, with another it is Y, with a third it is Z, and so forth. As will be described, the pressure in air bladder 30 affects the extent to which a thermal bladder is pressed against the person's knee. By using valves of different levels, the amount of pressure exerted can be controlled.

Referring to FIGS. 4 and 5, brace 20 preferably comprises a thermal bladder 70, partially schematically shown. Thermal bladder 20 includes sheets of flexible, liquid impervious material which are sealed around the margins and also in a grid to create an array of individual cells filled with a thermally responsive medium 72, such as a water/isopropyl alcohol mixture or a commercially available gel, such as Elasto Gel, from Technologies Inc. of Kansas City, Mo. The sheets defining bladder 70 may be made, for example, of polyethylene, polyvinylchloride, polyurethane, natural or synthetic rubber. Sealing may be accomplished by heat, welding, gluing, and the like. Thermal bladder 70 may reside freely in its pocket or be attached with snaps, or a Velcro-like fastening system, as depicted toward the right in FIG. 4.

Figure 11:
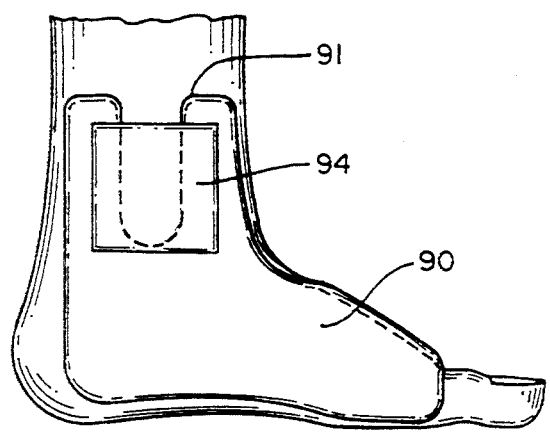
FIG. 11 depicts a first preparatory wrap on a person's ankle.
Figure 12:
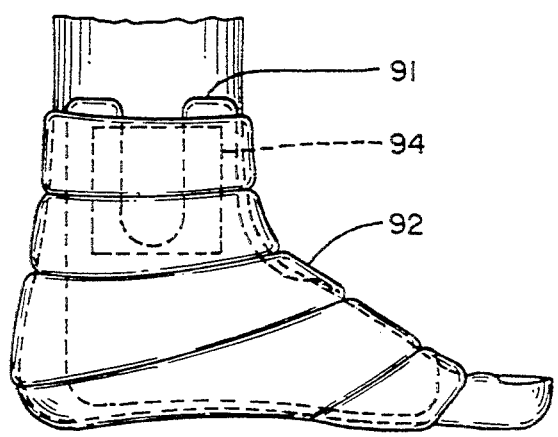
FIG. 12 depicts a second preparatory wrap on a person's ankle.

In certain instances it may be desirable to incorporate in the same brace two air bladders that exert different pressure levels. For example, on one's ankle, the pressure exerted by the air bag adjacent the foot could exert more pressure than the air bag adjacent the leg. Prior to applying such a brace, and referring to FIG. 11, a pad 90 is placed adjacent to the person's skin, which pad has a cutaway area 91. Pad 90 is preferably composed of rubber, felt or foam and is one quarter to one half inch thick. It is attached by using pre-wrap tape 92 (FIG. 12). Pad 90 is shaped to allow passage of edema from the injured area into the lymphatic system. A plastic or hard-cased sheet 94 is placed over area 91, covering but not touching the skin in such area.

Figure 13:
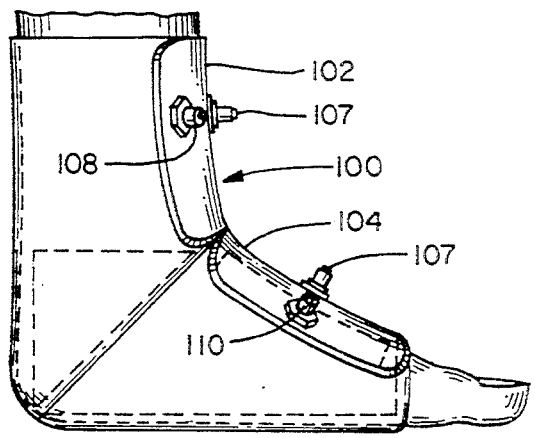
FIG. 13 depicts a second embodiment of the brace designed for application to a person's ankle.
Figure 14:
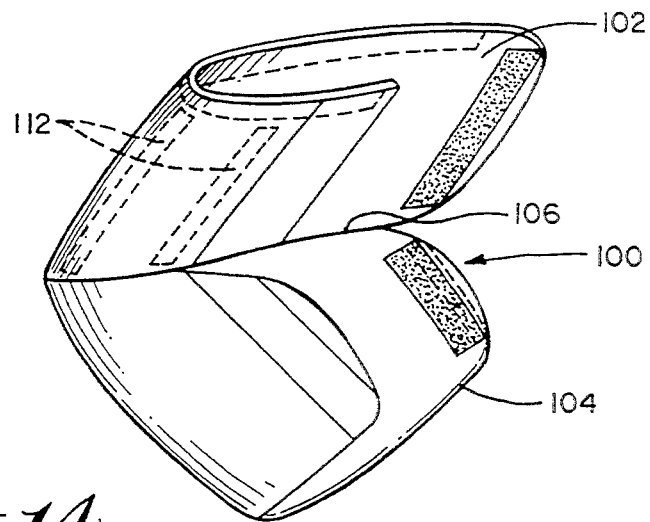
FIG. 14 is a perspective view of the ankle brace of FIG. 13.

Referring to FIGS. 13 and 14, a brace 100 incorporating the features of a second embodiment of the present invention is then applied. Brace 100 has two separate sections 102 and 104 connected at 106. Each of sections 102 and 104 has a construction generally corresponding to the first embodiment, except that each section has a single pocket. Each section is provided with snaps, or a Velcro-like fastening systems corresponding to those in the first embodiment. Each section is provided with an air inlet valve 107 generally the same as air inlet valve 40 in the first embodiment. Section 102 has a pressure-maintaining valve 108 and section 104 has a pressure-maintaining valve 110. Pressure maintaining valves have different pressure levels. The idea is to provide greater pressure distally than ventrally and thus force the swelling up the limb and back into the lymphatic system. As the person walks or moves, the movement provides a pneumatic pumping by increasing and releasing pressure as the body movement pushes out against the brace. As with the first embodiment, a thermal bladder can be associated with either or both sections 102 and 104. In the particular embodiment depicted in FIGS. 13 and 14, stays 112 are either sewn or glued in place, limiting its flexibility. Stays 112 may be composed of plastic or metal for example.

While, for purposes of illustration, a few preferred embodiments of this invention have been shown and described, other forms thereof will become apparent to those skilled in the art upon reference to this disclosure; and, therefore, it should be understood that any such departures from the specific embodiment shown and described are intended to fall within the spirit and scope of this invention.

What is claimed is:

1. A brace having a shape to match a predetermined body part, comprising means forming a flexible pocket, a thermal bladder in said pocket that selectively provides heating or cooling, a pressure bladder in said pocket, first valve means associated with said pressure bladder for introducing a gas therein from a gas source, and second valve means associated with said pressure bladder for automatically maintaining the gas pressure in said bladder at a predetermined level said second valve means being readily replaceable with a plurality of other second valve means respectively having a plurality of different predetermined levels.

2. The brace of claim 1, wherein said pocket is comprised of a first flexible sheet of insulating material and a flexible second sheet of absorbent material adapted to be placed in contact with the body part, means connecting said sheets to form said pocket.

3. The brace of claim 2, and further comprising means for selectively closing said pocket.

4. The brace of claim 1, wherein said brace further comprises a second pocket and a second pressure bladder in said second pocket.

5. The brace of claim 1, wherein said thermal bladder includes an outer shell comprised of flexible, liquid-pervious material sealed along a plurality of lines to create an array of cells, and a thermally responsive liquid in said cells.

6. The brace of claim 5, wherein said thermally responsive medium is a water/isopropyl alcohol mixture.

7. The brace of claim 1, wherein said brace has a shape to match a persons knee.

8. A brace having a shape to match a predetermined body part comprising means forming first and second flexible pockets, a thermal bladder in each of said pockets that selectively provides heating or cooling, first and second pressure bladders respectively in said pockets, first valve means associated with each of said pressure bladders for introducing a gas therein from a gas source, second valve means associated with said first pressure bladder for automatically maintaining the gas pressure in said first bladder at a predetermined first level, third valve means associated with said second pressure bladder for automatically maintaining the gas pressure in said second bladder at a predetermined second level said second and third valve means being readily replaceable with a plurality of other second and third valve means respectively having a plurality of different predetermined levels.

* * * * *